(12) United States Patent
Belei (10) Patent No.: US 9,833,209 B2
(45) Date of Patent: Dec. 5, 2017

(54) CAMERA-BASED VISUAL ADJUSTMENT OF A MOVABLE X-RAY IMAGING SYSTEM

(71) Applicant: KONINKLIJKE PHILIPS N.V., Eindhoven (NL)

(72) Inventor: Peter Belei, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 257 days.

(21) Appl. No.: 14/420,973

(22) PCT Filed: Aug. 13, 2013

(86) PCT No.: PCT/IB2013/056623
§ 371 (c)(1),
(2) Date: Feb. 11, 2015

(87) PCT Pub. No.: WO2014/027312
PCT Pub. Date: Feb. 20, 2014

(65) Prior Publication Data
US 2015/0230768 A1  Aug. 20, 2015

Related U.S. Application Data

(60) Provisional application No. 61/684,203, filed on Aug. 17, 2012.

(51) Int. Cl.
*A61B 6/08* (2006.01)
*A61B 6/00* (2006.01)

(52) U.S. Cl.
CPC ............ *A61B 6/463* (2013.01); *A61B 6/4405* (2013.01); *A61B 6/4441* (2013.01); *A61B 6/547* (2013.01); *A61B 6/587* (2013.01)

(58) Field of Classification Search
CPC ....... A61B 6/463; A61B 6/587; A61B 6/4405; A61B 6/547; A61B 6/4441
(Continued)

(56) References Cited

U.S. PATENT DOCUMENTS 6,079,876 A * 6/2000 Schuetz ................ A61B 6/08
378/205
6,120,180 A   9/2000 Graumann
(Continued)

FOREIGN PATENT DOCUMENTS

DE    4423359 A1   1/1996
DE   19746093 A1   5/1999
(Continued)

OTHER PUBLICATIONS

Barbe et al, "Evaluation of the Efficiency of the Zero-Dose-C-Arm Navigation Approach", Z Orthop Unfall, vol. 148, 2010, pp. 554-558.
(Continued)

*Primary Examiner* — Courtney Thomas (57) ABSTRACT

The present invention relates to the adjustment of movable X-ray imaging systems for aligning an object of interest and an X-ray imaging arrangement and comprises an X-ray imaging arrangement with a source and detector, at least one camera, a data processor; and a display, wherein the display is configured to display a graphical representation of at least one reference point in a first image at least partly overlaid with an actual image provided by the at least one camera to guide an alignment movement of the X-ray source and/or the X-ray detector and an object in relation to each other after an intermediate displacement.

14 Claims, 8 Drawing Sheets

(58) Field of Classification Search
USPC .................................. 378/193–198, 62, 205
See application file for complete search history.

(56) References Cited

U.S. PATENT DOCUMENTS

| | | | |
|---|---|---|---|
| 7,477,723 B2 | 1/2009 | Kamegawa et al. | |
| 7,766,548 B2 | 8/2010 | Dehler et al. | |
| 2002/0150215 A1 | 10/2002 | Barnes et al. | |
| 2004/0122311 A1* | 6/2004 | Cosman | A61B 6/5247 600/427 |
| 2005/0013410 A1* | 1/2005 | Hornegger | A61B 6/06 378/151 |
| 2005/0251914 A1 | 11/2005 | Schaller et al. | |
| 2007/0135803 A1* | 6/2007 | Belson | A61B 1/00154 606/1 |
| 2008/0094396 A1 | 4/2008 | Sabczynsdi et al. | |
| 2008/0198971 A1* | 8/2008 | Schulze-Ganzlin | A61B 6/145 378/170 |
| 2009/0015680 A1 | 1/2009 | Harris et al. | |
| 2009/0028291 A1* | 1/2009 | Graumann | A61B 6/00 378/19 |
| 2010/0299014 A1* | 11/2010 | Bouvier | A61B 6/4405 701/25 |

FOREIGN PATENT DOCUMENTS

| | | |
|---|---|---|
| DE | 102005052784 B3 | 7/2007 |
| DE | 102005052786 B3 | 7/2007 |
| EP | 2380496 A1 | 10/2011 |
| WO | 2012156861 A1 | 11/2012 |
| WO | 2013140293 A1 | 9/2013 |
| WO | 2013144841 A2 | 10/2013 |
| WO | 2013190409 A2 | 12/2013 |
| WO | 2014013393 A2 | 1/2014 |

OTHER PUBLICATIONS

Navab et al, "Visual Servoing for Intraoperative Positioning and Repositioning of Mobile C-Arms", MICCAI, 2006, p. 551-560.

* cited by examiner

CAMERA-BASED VISUAL ADJUSTMENT OF A MOVABLE X-RAY IMAGING SYSTEM

CROSS-REFERENCE TO PRIOR APPLICATIONS

This application is the U.S. National Phase application under 35 U.S.C. §371 of International Application Serial No. PCT/IB2013/056623, filed on Aug. 13, 2013, which claims the benefit of U.S. Application Ser. No. 61/684,203, filed on Aug. 17, 2012. These applications are hereby incorporated by reference herein.

FIELD OF THE INVENTION

The present invention relates to the adjustment of movable X-ray imaging systems, and relates in particular to a movable X-ray imaging system for aligning an object of interest and an X-ray imaging arrangement in relation to each other, a method for alignment in X-ray imaging, as well as to a computer program element and a computer readable medium.

BACKGROUND OF THE INVENTION

In movable X-ray imaging systems, for example mobile C-arm systems, the positioning is of importance for optimal image quality and also for the ease of use. As an example, during an operation or intervention, the X-ray imaging system can be moved at least partially for different purposes. For example, a fluoroscopy projection image is acquired, and the X-ray imaging system is moved to a different position afterwards in order to provide free space for the operation procedure. The X-ray imaging system can also be moved to a different position for acquiring different images from different directions. After or during an operation, it may further be necessary to acquire a further image of the same region of interest, preferably in at least a similar viewing position. Therefore, the movable X-ray imaging arrangement is moved once again to the initial position. As an example, this may happen multiple times during especially longer operations. In order to be able to achieve the same or at least nearly the same position, external position tracking is used, for example described in U.S. Pat. No. 7,766,548. However, it has been shown that external position tracking devices mean additional equipment costs and increased equipment clutter in the operation room and sometimes even have workflow limitations. Further, also integrated sensors are used. However, integrated sensors also mean additional costs and require the operator's attendance and knowledge for aligning and positioning.

SUMMARY OF THE INVENTION

Thus, there is a need to provide a facilitated alignment and positioning for a movable X-ray imaging system with reduced hardware requirements, allowing an intuitive operation.

The object of the present invention is solved by the subject-matter of the independent claims, wherein further embodiments are incorporated in the dependent claims.

It should be noted that the following described aspects of the invention apply also for the movable X-ray imaging system for aligning an object of interest and an X-ray imaging arrangement in relation to each other, for the method for aligning an X-ray imaging, as well as for the computer program element and the computer readable medium.

According to a first aspect of the present invention, a movable X-ray imaging system for aligning an object of interest and an X-ray imaging arrangement in relation to each other is provided that comprises an X-ray imaging arrangement with an X-ray source and an X-ray detector, at least one camera, a data processor, and a display. The at least one camera is either attached to the X-ray imaging arrangement or is attachable to the object of interest. The at least one camera is further configured to provide a first image of at least one reference point. The data processor is configured to relate the first image to first projection parameters of a first X-ray image of the object of interest in relation to the object. The projection parameters relate to different degrees of freedom and comprise at least one of the group of spatial projection position, distance to the object, viewing direction or projection angle, and viewing field. For an acquisition of at least one further X-ray image in a projection coincident with the first projection parameters angle of the first X-ray image, the display is configured to display at least a graphical representation of the at least one reference point in the first image at least partly overlaid with an actual image provided by the at least one camera to guide an alignment movement of the X-ray source and/or the X-ray detector and the object in relation to each other after an intermediate displacement.

In one example, the projection parameters comprise the viewing direction, allowing translational movement along the projection axis and perpendicular to it. In another example, the projection parameters comprise the viewing position, allowing a rotation around the point in space. In another example, the projection parameters may comprise five degrees of freedom, wherein the rotation around the viewing direction can be achieved manually or controlled by the user. In another example, six degrees of freedom, three translational and three rotational, are covered by the projection parameters.

The graphical representation is displayed in the same geometric relation to the second image as the at least one reference point in the first image. In other words, the graphical representation is displayed in the same geometric relation to the display area of the display.

The graphical representation is a reference image stored for the combined display with the second image. The reference image may also be the first image itself, showing the at least one reference point.

The display of a reference point, or a reference image, shows a difference between the target position and the actual position in an intuitive way by combining the display of the reference point, or the reference image, with the second image. Thus, an easy retrievable way for fine positioning of an X-ray source is provided, for example for positioning a C-arm.

The system thus comprises two movable parts that need to be (re-)aligned after moving, i.e. the X-ray imaging arrangement and the object of interest. The at least one camera of the system is integrated such that it is movable either together with the object of interest or together with the X-ray imaging arrangement. For the alignment, the camera provides an actual image of the at least one reference point that is also visible on the overlaid image, or in the combined image. During the alignment, the camera is moved in relation to the other part, i.e. a relative camera movement occurs.

A support structure may be provided, which is configured to provide a relative movement between an object of interest, an X-ray source and/or the X-ray detector.

According to an exemplary embodiment, the display is configured to display the graphical representation, a) in form of at least one manually applied marker, wherein the display is configured to display the at least one marker at least partly overlaid with the actual image, and/or b) in form of the first image itself, wherein the display is configured to display the first image at least partly overlaid with the actual image.

The graphical representation may be a manually applied outline or mark made on the displayed first image, for example directly on the screen. The manual graphical element can be stored separately to be shown overlaid to the second image.

According to an exemplary embodiment, the at least one camera remains in known spatial relation to the X-ray source and/or the X-ray detector, and the at least one reference point remains in constant spatial relation to the object of interest at least during the relative movement.

According to an alternative exemplary embodiment, the at least one camera is temporarily fixedly mounted in relation to the object of interest, and the at least one reference point remains in known spatial relation to the X-ray source and/or the X-ray detector during the relative movement.

For example, in the first case, the at least one camera is fixedly mounted in relation to the X-ray source and/or the X-ray detector. In the second case, for example, the at least one reference point remains in constant spatial relation to the X-ray source and/or the X-ray detector during the relative movement.

The movable X-ray imaging system may be provided as a positionable X-ray acquisition device. The movable X-ray imaging system is a mobile X-ray system with a movable support structure attached to a mobile stand in one example. The support structure may be a C-arm system structure.

For example, alternatively or in addition, the support structure comprises an object support, which is configured to move the object in relation to the X-ray source and/or the X-ray detector. Thus, the system comprising the X-ray imaging arrangement can be moved; or, in addition or alternatively, the object can be moved. In any case, a relative movement occurs.

According to an exemplary embodiment, for the acquisition of further X-ray images, for a first approximation, a support structure is movable such that the X-ray source and/or the X-ray detector are within a predetermined range of the position of the first projection. The support structure may comprise at least one movable joint with detectable joint positions and is movable to a predetermined range of matching joint positions in a second approximation. The display may be configured to display at least the graphical representation of the reference point in the first image overlaid with the actual image for the alignment as a third approximation.

The first approximation is a rough approximation, the second approximation is a medium approximation, and the third approximation is a fine approximation.

For example, the first image is shown overlaid with the second image in a semi-transparent manner.

According to an exemplary embodiment, at least two reference points are provided, or at least three reference points, or more than three reference points.

For example, one reference point is sufficient to repositioning regarding translational movement related to the camera view. Further, a second reference point is required when orientation or a distance to object should also be detected and adjusted. A third reference point allows for inclination (or distortion) of the imaging plane the plane of the reference points.

According to an exemplary embodiment, the at least one reference point is provided on the object of interest. Further the at least one reference point may also be provided on a reference field provided in an examination room.

For example, the one or more reference points are provided as indicators on the object's surface.

According to an exemplary embodiment, the at least one reference point is provided as a laser projection.

The laser projection may comprise more than two reference points, for example three or four points. The laser projection may comprise a frame projection.

The graphical representation may be a manually applied outline of the laser projection stored as part of the reference image.

The camera may be a video camera acquiring images in the visible light range. The camera may also be an infrared camera acquiring infrared data transferred into a visible image.

A plurality of cameras may be provided at different locations to provide a plurality of first images and a plurality of actual images combined, for example, pairwise.

The X-ray source and the X-ray detector are provided as an image acquisition arrangement that is positionable in relation to the object to acquire the image data of the object from different directions.

According to an exemplary embodiment, for the alignment movement, the X-ray source and/or the X-ray detector are movable in relation to the object in at least two movement directions. First movement direction indicators are provided on the X-ray source and/or the X-ray detector, visible to the user to indicate possible movement directions in relation to the object. On the display, second movement direction indicators are provided in relation to the displayed image date of the object to indicate the possible movement directions of the image acquisition arrangement in relation to the object.

According to an exemplary embodiment, the first movement direction indicators are provided for a movement plane, wherein the first movement direction indicators are provided as a planar orientation coding, comprising one of the groups of a) clock positions, b) cardinal directions, and c) colours on a chromatic circle.

According to a second aspect, a method for aligning an X-ray imaging is provided, comprising the following steps:
a) acquiring a first image of at least one reference point with at least one camera;
b) acquiring a first X-ray image of the object of interest with first projection parameters in relation to the object; wherein the projection parameters relate to different degrees of freedom and comprise at least one of the group of spatial projection position, distance to the object, viewing direction or projection angle, and viewing field; c) relating the first image to the first projection parameters of the first X-ray image in relation to the object;
d) acquiring an actual image with the at least one camera;
e) displaying at least a graphical representation of the at least one reference point in the first image at least partly overlaid with the actual image for guiding an alignment movement of the X-ray source and/or the X-ray detector and the object in relation to each other after an intermediate displacement;
f) aligning moving of the X-ray source and/or the X-ray detector and the object in relation to each other for an acquisition of at least one further X-ray image in a projection coincident with the first projection parameters of the first X-ray image after an intermediate displacement, based on the displayed overlaid images.

Either i) the at least one camera is fixedly mounted in relation to the X-ray source and/or the X-ray detector, and the at least one reference point remains in constant spatial relation to the object of interest at least during the relative movement; or ii) the at least one camera is temporarily fixedly mounted in relation to the object of interest, and the at least one reference point remains in constant spatial relation to the X-ray source and/or the X-ray detector during the relative movement.

For example, the graphical representation is the first image itself, and the first image is overlaid in a manner differing from the actual image in step e). For example, the first image is provided as a grey scale image overlaid on the actual image provided in colour. For example, the actual image is displayed overlaid with the first image at least successively in a first and a second scale providing an increasing magnification factor for an increasing approximation of alignment.

According to an aspect of the present invention, an image with distinguishable features is acquired in the position where the first X-ray image is acquired. Since either the reference points in the image, or the camera is moved together with the relative movement of the X-ray imaging system to the object, the position of the first X-ray image can be found by searching for a position in which the same or similar image can be acquired. Thus, by displaying the first image, or at least some basic and easy retrievable structures shown in the first image, a visual guiding aid is provided for aligning the X-ray imaging system, providing an intuitive and easy retrievable feedback to where the X-ray imaging system has to be moved for proper aligning. Thus, instead of any calculated vectors or alternated positioning, the alignment is only based on the visual detection of any predetermined structure that remains more or less constant. For example, this could be the adjacent area or immediate surroundings of an operational field, as well as the image comprises features that can act as reference points. For example, in case of an ongoing and longer interventional procedure, fixedly provided interventional tools, such as brackets or clamps holding open an operational field, can act as reference points. By providing content of the first image together with the actual, i.e. second image, a direct user interaction is possible, allowing a robust and facilitated and thus rather fast way of aligning the X-ray imaging system. In particular, it must be noted that the display for displaying the second image and the reference point of the first image is usually available anyhow, which is also the case for video camera equipment. Nevertheless, for the camera it can be relied on rather simple and thus cheap cameras that can be attached to the detector housing, for example. Further, also a data processor with a storage is usually at hand in an X-ray imaging system. In other words, the system and method according to the present invention is based mostly on equipment that is provided in an X-ray imaging arrangement and that does not involve any complicated image processing steps.

It must be noted that examples are described with reference to different subject-matters. Some examples are described in relation with the system, and some examples are described in relation with the method. However, a person skilled in the art understands that in addition to any combination of features belonging to one type of subject-matter, also any combination between features relating to different subject-matters are provided.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1A:
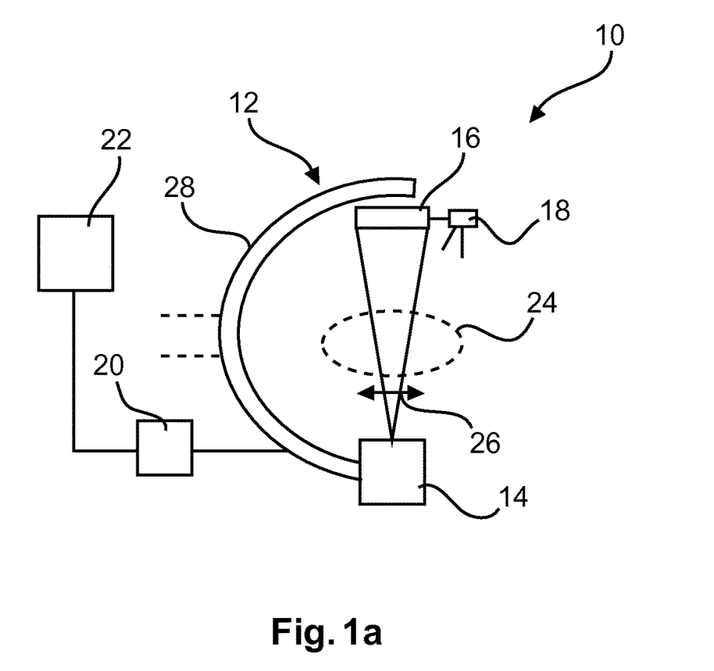
FIG. 1 shows a movable X-ray imaging system in a schematic setup in a first example in FIG. 1A and a second example in FIG. 1B.
Figure 1B:
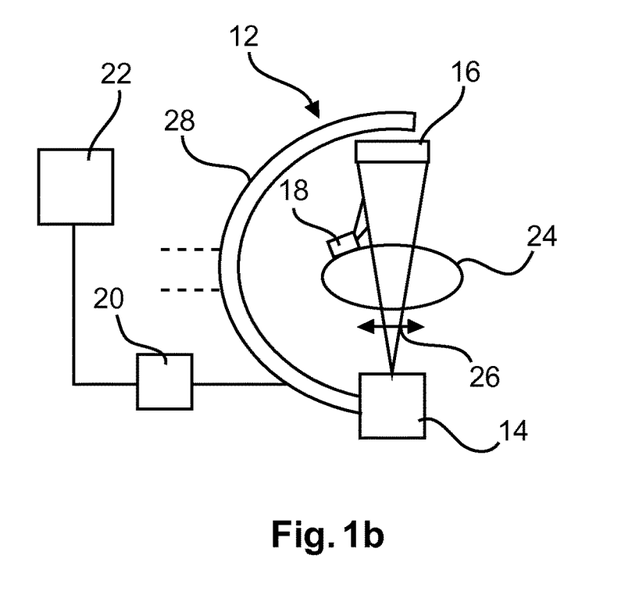

FIG. 1 shows a movable X-ray imaging system 10 for aligning an object of interest in an X-ray imaging arrangement in relation to each other. The system comprises an X-ray imaging arrangement 12 with an X-ray source 14 and an X-ray detector 16. Further, at least one camera 18 is provided, together with a data processor 20 and a display 22. In FIG. 1A, the camera 18 is attached to the X-ray imaging arrangement. In FIG. 1B, the same reference numbers have been used for the same features of the movable X-ray imaging system 10. In FIG. 1B, the at least one camera 18 is attachable to an object of interest 24.

With reference to both examples, the at least one camera 18 is configured to provide a first image of at least one reference point. The data processor 20 is configured to relate the first image to first projection parameters of a first X-ray image of the object of interest in relation to the object. The projection parameters relate to different degrees of freedom and comprise at least one of the group of spatial projection position, distance to the object, viewing direction or projection angle, and viewing field.

For an acquisition of at least one further X-ray image in a projection coincident with the first projection parameters of the first X-ray image, the display 22 is configured to display at least a graphical representation of the at least one reference point in the first image at least partly overlaid with an actual image provided by the at least one camera 18 to guide an alignment movement of the X-ray source and/or the X-ray detector and the object in relation to each other after an intermediate displacement.

As a schematic indication only, a double arrow 26 indicates the relative movement of the X-ray imaging arrangement 12 and the object 24.

For example, the X-ray imaging arrangement is movable, whereas the object remains fixed, at least temporarily fixed, for example on a patient support table.

According to a further example, it is the object of interest on a movable support that provides the relative movement, whereas the X-ray imaging arrangement with X-ray source and X-ray detector remains fixed.

For example, the X-ray source 14 and the X-ray detector 16 are mounted to a C-arm structure 28, which C-arm structure may be movably supported.

The display 22 is configured to display the graphical representation, for example in form of at least one manually applied marker, wherein the display is configured to display the at least one marker at least partly overlaid with the actual image.

In another example, the display is configured to display the graphical representation in form of the first image itself, wherein the display is configured to display the first image and at least partly overlaid with the actual image.

The graphical representation may be a manually applied outlining or mark made on the displayed first image. The manual graphical element can be stored separately to be shown overlaid to the second image.

In the example of FIG. 1A, the at least one camera 18 remains in known spatial relation to the X-ray source and/or the X-ray detector. The at least one reference point remains in constant spatial relation of the object of interest at least during the relative movement. For example, the at least one reference point is provided on the object's surface.

In the example of FIG. 1B, the at least one camera is temporarily fixedly mounted in relation to the object of interest, and the at least one reference point remains in known spatial relation to the X-ray source and/or the X-ray detector during the relative movement.

In case of a motorized C-arm, it could also be possible to provide the at least one camera fixed, while moving the C-arm, and thus the X-ray source and the X-ray detector, with known parameters, which allow the determination of the exact position of at least one camera in relation to the X-ray source and X-ray detector, since their movement in space is known.

Figure 2A:
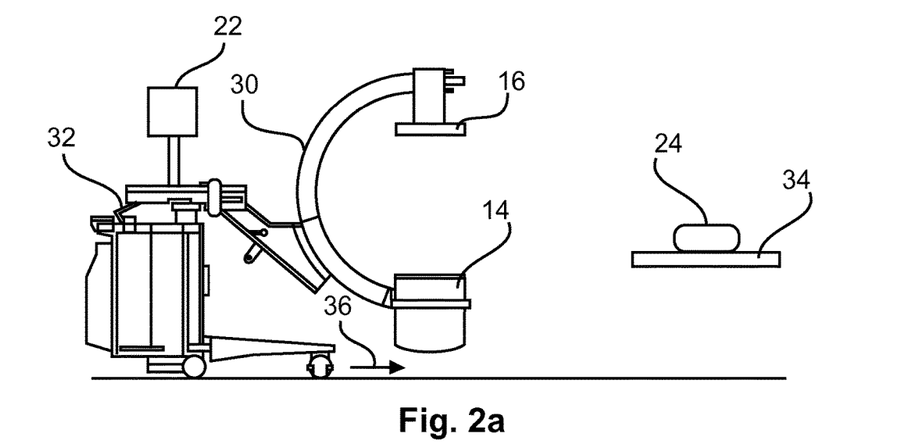
FIG. 2 shows a first approximation in FIG. 2A of the X-ray imaging arrangement and an object, and a second approximation in FIG. 2B, and a third approximation in FIG. 2C.
Figure 2B:
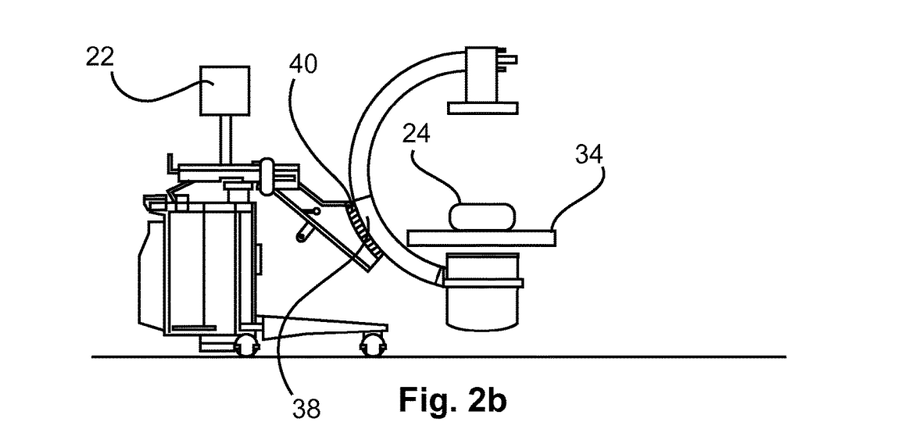
Figure 2C:
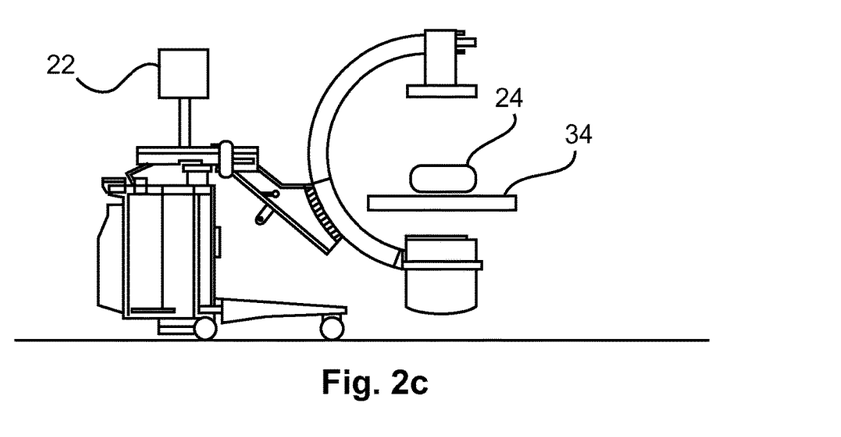

The movable X-ray imaging system may be provided as a positional X-ray acquisition device, for example as a mobile X-ray system with a movable support structure 30 attached to a mobile stand 32, as shown in FIGS. 2A to 2C.

According to a further example, an object support 34 is provided, which may be configured to remain constant, i.e. remain unmoved, during the procedure, or which may be configured to move the object, for example a patient, in relation to the X-ray source and/or the X-ray detector.

For the alignment movement of the X-ray source 14 and the X-ray detector 16 in relation to the object 24, the display 22 may be configured to display the actual image overlaid with at least one graphical representation of the at least one reference point in the first image at least successively in a first and a second scale, providing an increasing magnification factor for an increasing approximation of alignment.

For example, the camera is provided with a wide-angle lens for acquiring image in a surrounding area of the reference point. Further, the camera may also be equipped with a light source for acquiring images at a dark environment.

Thus, an increasing approximation is possible, which is also described with reference to FIGS. 2A to 2C.

For a first approximation, shown in FIG. 2A, the support structure 30 together with a movable stand 32, is movable such that the X-ray source 14 and/or the X-ray detector 16 are within a predetermined range of the position of the first projection. For example, in FIG. 2A, the movable stand 32 is moved towards the right, as indicated with arrow 36, for bringing the X-ray imaging arrangement in a position, i.e. approximately equal to the first position, in which a first X-ray image has been acquired beforehand. The first approximation's result is shown in FIG. 2B. The support structure 30 may comprise at least one movable joint 38, for example sliding shoe-like attachment of the C-arm structure, with detectable joint positions, indicated by a scaling structure 40, and wherein the support structure is movable to a predetermined range of matching joint positions in a second approximation (not further shown). As a third approximation, shown in FIG. 2C, the display is configured to display at least the graphical representation of the reference point in the first image overlaid with the actual image for the alignment as a third approximation (not further shown).

According to a further example, although not further shown, at least two reference points are provided, and in a further example, at least three reference points are provided, and in a still further example, even more than three reference points are provided (not further shown).

According to an example, the at least one reference point is provided on the object of interest, for example, the one or more reference points are provided as indicators on the object's surface.

Figure 3:
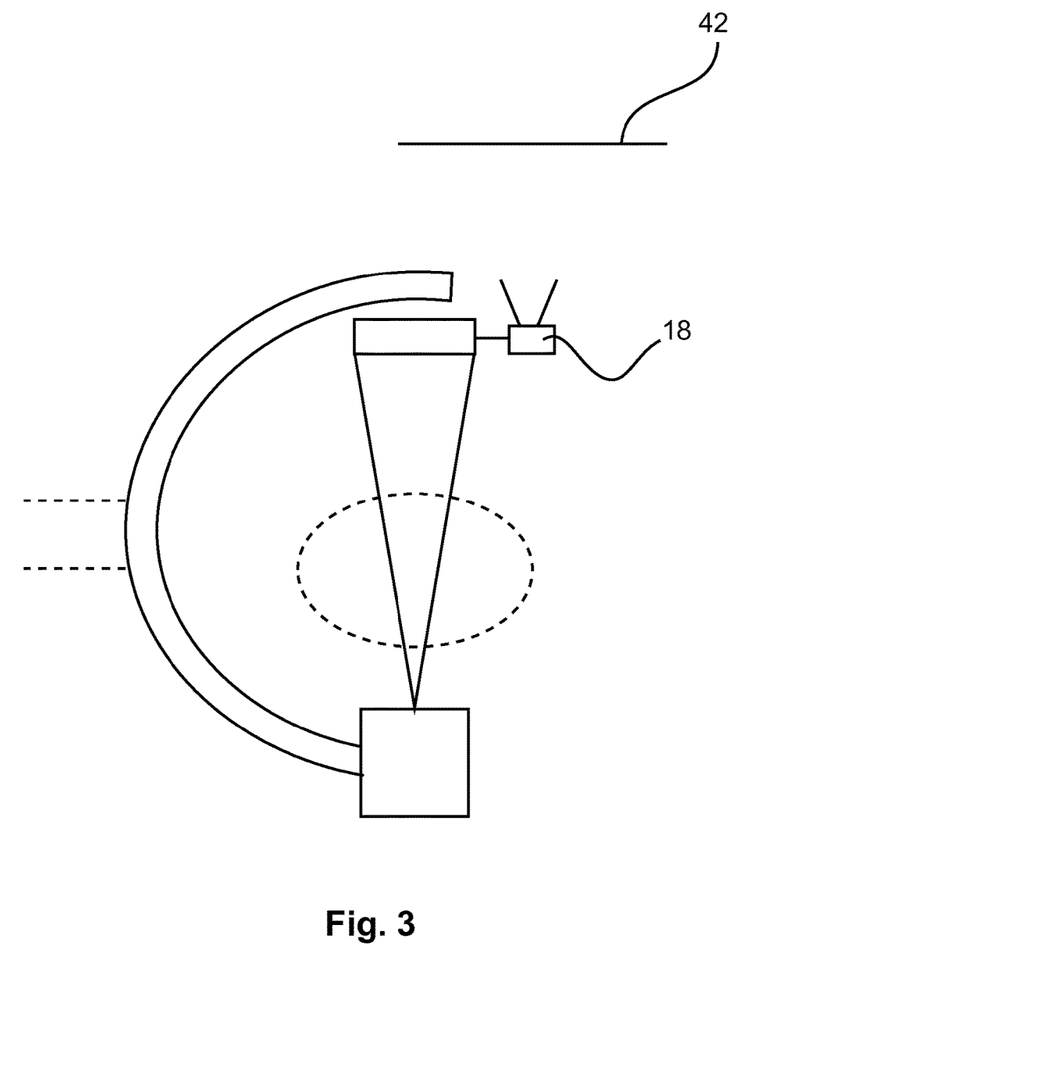
FIG. 3 shows a further example of a movable X-ray imaging system.

However, with reference to FIG. 3, the at least one reference point may also be provided on a reference field 42, provided in an examination room, for example as a reference field attached to a ceiling surface. Thus, the reference field 42 can be acquired by the at least one camera 18, providing information about alignment or misalignment.

Figure 4:
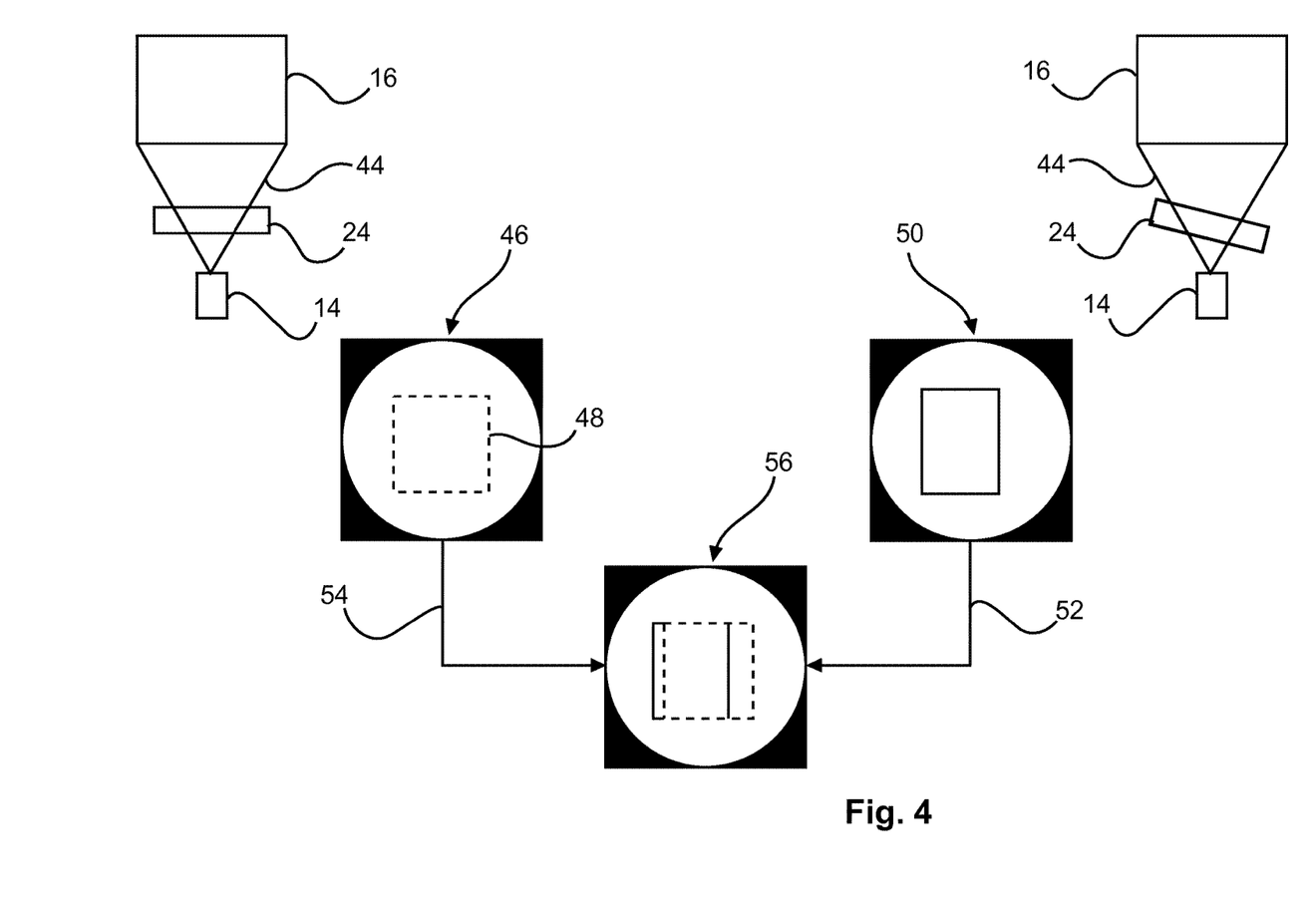
FIG. 4 schematically shows further examples of a movable X-ray imaging system.

As shown in FIG. 4, the at least one reference point may be provided as a laser projection 44, for example as used for indicating a possible X-ray field provided by the X-ray source 14, and detected by the X-ray detector 16. In FIG. 4, the object 24 is indicated with a rectangle. Further, it is noted that the device for generating the laser projection 44 is not further shown. The laser projection may comprise more than two reference points, for example three or four points, for example in case of a frame projection.

As further shown in FIG. 4, the situation when acquiring the first X-ray image is indicated in the upper left corner, and the respectively display is shown as schematic display setup 46. As indicated with a rectangular structure 48, the laser projection in form of a frame is manually outlined to provide the graphical representation.

In order to align the X-ray source 14 and the X-ray detector 16 in relation to the object 24 to be in accordance with the positioning of the first X-ray imaging acquisition, for example for a acquiring a further X-ray image, the camera (not further shown) provides an image of the actual situation, as indicated with a further image setup 50 in the right middle portion of FIG. 4, the schematic setup of the actual situation shown in the upper right corner of FIG. 4.

By providing the actual image arrangement 50, which providing is indicated with arrow 52, and by also providing the manually applied outline 48, indicated with a second arrow 54, an overlay image setup 56 can be achieved, showing the respective misalignment that still needs some further alignment, namely a correction of the inclined arrangement of the object 24.

Figure 5:
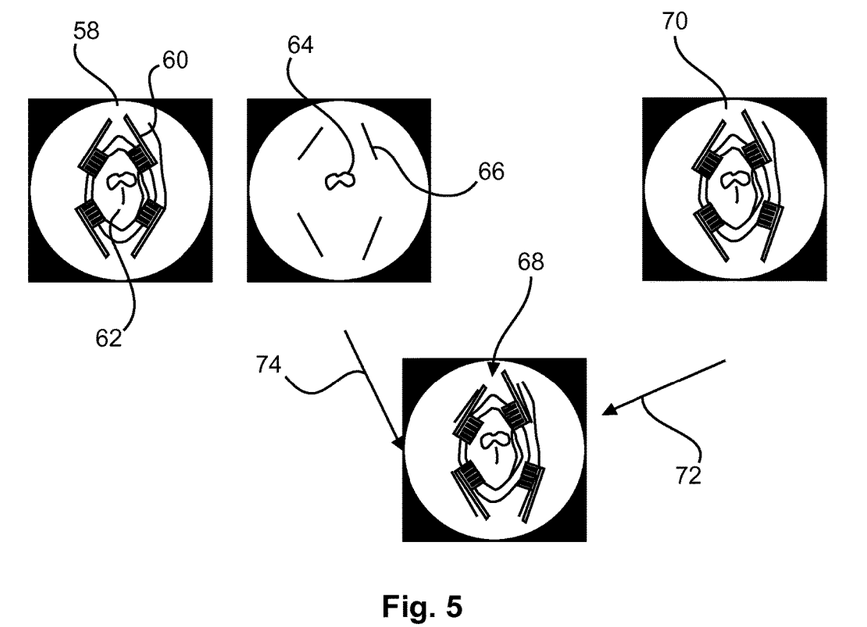
FIG. 5 shows display presentations in relation with a still further example of a movable X-ray imaging system.

FIG. 5 shows a further schematic setup for the alignment movement. An image 58 indicates clamps 60 holding open an operational field 62. As a manually applied outline, a manually applied marking 64 is provided, together with the angular arrangement of the clamps 60, represented by centre lines 66. These manually applied outlines can then be used further, for example as reference points in a further image setup 68, which is a combination of the result of the image 58, in combination with an actual image 70, provided for the combination of image setup 68, as indicated with first arrow 72 and second arrow 74, the latter indicating the provision of the manually applied outline structures.

Figure 6:
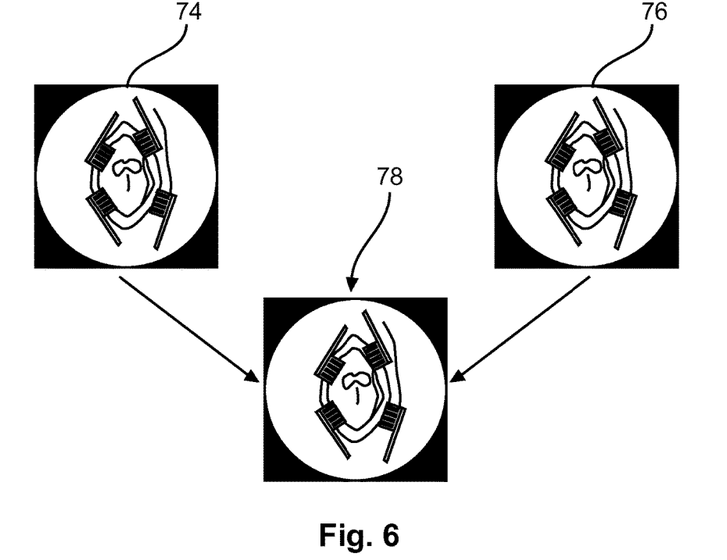
FIG. 6 shows a further example of display presentations.

A further example is shown in FIG. 6, where a first image 74 is shown in the upper left corner, and a second image, i.e. an actual image 76 is shown in the upper right corner. In a further step, the two images are forming a combined overlay 78, for example for fine positioning of a C-arm.

According to a further example (not further shown), sensors are provided for detecting a degree of the relative movement that is not detectable by the camera.

For example, the camera is a video camera acquiring images in a visible light range.

Figure 7:
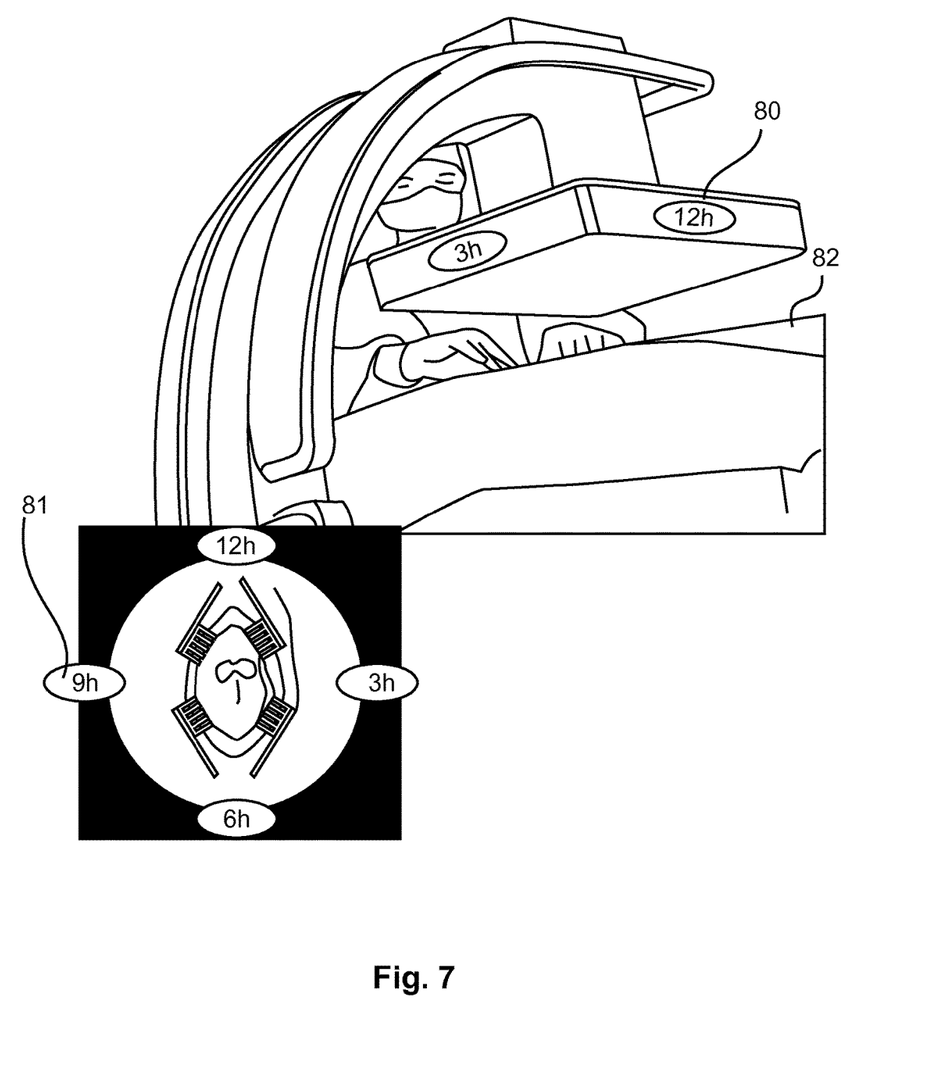
FIG. 7 shows a further example of a movable X-ray imaging system comprising movement direction indication.

FIG. 7 shows a further example, wherein, for the alignment movement, the X-ray source and the X-ray detector are movable in relation to the object in at least two movement directions. Further, first movement direction indicators 80 are provided on the X-ray detector visible to the user, and/or on the X-ray source, to indicate possible movement directions in relation to the object, for example a patient under a drape structure 82.

Further, also on the display, second movement direction indicators 81 are provided in relation to the displayed image data of the object to indicate the possible movement directions of the image acquisition arrangement in relation to the object.

The first movement direction indicators 80 may be provided as adaptable movement direction indicators. The first movement direction indicators 80 may be provided such that a bijective identification of the complementary direction is possible. For example, the first movement direction indicators 80 are provided as denominated symbols, such that the movement directions are addressable with unambiguous messages.

For example, the first movement direction indicators 80 are provided for a movement plane, wherein the first movement direction indicators 80 are provided as a planar orientation coding, such as, for example, clock positions, as shown. As a further example, cardinal directions can be used, or colours on a chromatic circle.

The movement direction indicators provide the possibility for an error-free and robust communication between the surgeon and the operating stuff for moving the X-ray imaging system.

Figure 8:
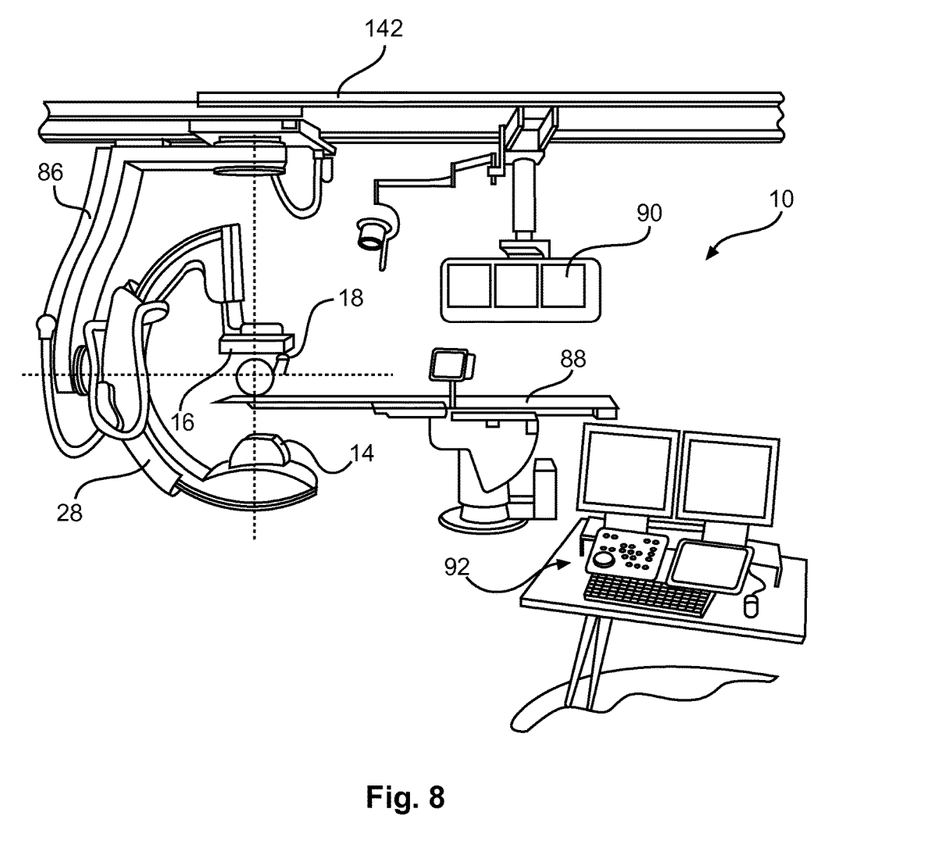
FIG. 8 shows a further example of movable X-ray imaging system in relation with other equipment in an interventional room.

FIG. 8 shows a further example of the movable X-ray imaging system 10, where the X-ray source 14 and the X-ray detector 16 are mounted to the ends of a C-arm structure with the C-arm 28, mounted by movable support structure 86. Further, also a patient table 88 and a display arrangement 90 is shown, in combination with a control unit 92 (not further explained).

Figure 9:
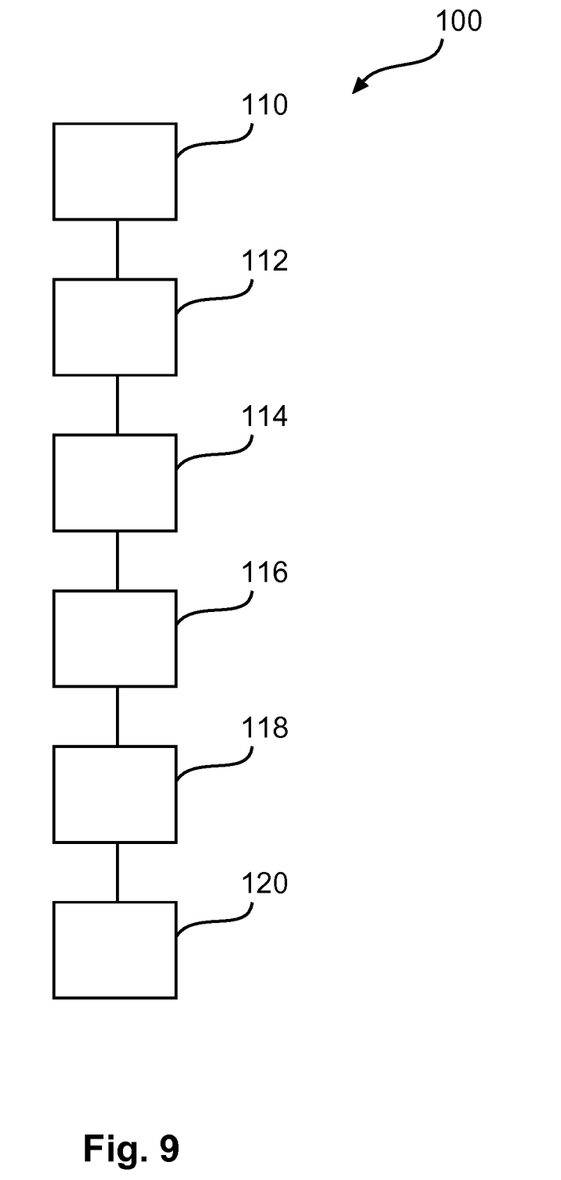
FIG. 9 shows basic steps of an exemplary method.

As shown in FIG. 9, also a method 100 for alignment in X-ray imaging is provided, comprising the following steps: In step a), a first image of at least one reference point is acquired 110 with at least one camera. In step b), a first X-ray image of the object of interest is acquired 112 with first projection parameters in relation to the object. The projection parameters relate to different degrees of freedom and comprise at least one of the group of spatial projection position, distance to the object, viewing direction or projection angle, and viewing field. Next, in step c), the first image is related 114 to the first projection parameters of the first X-ray image in relation to the object. Further, in step d), an actual image is acquired 116 with the at least one camera. In the following step e), at least a graphical representation of the at least one reference point in the first image is displayed 118, and at least partly overlaid with the actual image for guiding an alignment movement of the X-ray source and/or the X-ray detector and the object in relation to each other after an intermediate displacement. In step f), an aligning moving 120 of the X-ray source and/or the X-ray detector and the object in relation to each other is provided, for an acquisition of at least one further X-ray image in a projection coincident with the first projection parameters of the first X-ray image after an intermediate displacement, based on the displayed overlaid images.

In a first case, the at least one camera is fixedly mounted in relation to the X-ray source and/or the X-ray detector, and the at least one reference point remains in constant spatial relation to the object of interest at least during the relative movement.

In a second case, the at least one camera is temporarily fixedly mounted in relation to the object of interest, and the at least one reference point remains in constant spatial relation to the X-ray source and/or the X-ray detector during the relative movement.

For example, in case there is no functionality implemented to digitally readout and store joint positions, for instance when using traditional mobile C-arms, the system operator recalls the joint positions, using the attached scales before making the fine position step using the "eye catch" functionality. In another version, the lens of the camera may be of "fish eye" type, as these provide a wider field of view, and therefore would enable more image information which potentially increases positioning accuracy of the fine positioning step using the "eye catch" functionality.

In another version of the invention, the C-arm is equipped with multiple cameras (not further shown) along the C-arm. By matching all views of these cameras with the respective pre-stored picture of each camera for an X-ray projection position, or at least by matching the respective graphical representation of the reference points, the C-arm position could be recalled without any other additional position information such as joint positions.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A movable X-ray imaging system for aligning an object of interest and an X-ray imaging arrangement in relation to each other, the system comprising:
   an X-ray imaging arrangement with an X-ray source and an X-ray detector;
   at least one camera;
   a data processor; and
   a display;
   wherein the at least one camera i) is either attached to the X-ray imaging arrangement or ii) is attachable to the object of interest;
   wherein the at least one camera is configured to provide a first image of at least one reference point; wherein the data processor is configured to relate the first image to first projection parameters of a first X-ray image of the object of interest in relation to the object; wherein the projection parameters relate to different degrees of freedom and comprise at least one of the group of spatial projection position, distance to the object, viewing direction or projection angle, and viewing field; and
   wherein, for an acquisition of at least one further X-ray image in a projection coincident with the first projection parameters of the first X-ray image, the display is configured to display at least a graphical representation of the at least one reference point in the first image at least partly overlaid with an actual image provided by the at least one camera to guide an alignment movement of the X-ray source and/or the X-ray detector and the object in relation to each other after an intermediate displacement.

2. X-ray imaging system according to claim 1, wherein the display is configured to display the graphical representation
   a) in form of at least one manually applied marker; wherein the display is configured to display the at least one marker at least partly overlaid with the actual image; and/or
   b) in form of the first image itself; wherein the display is configured to display the first image at least partly overlaid with the actual image.

3. X-ray imaging system according to claim 1, wherein:
   i) the at least one camera remains in known spatial relation to the X-ray source and/or the X-ray detector; and the at least one reference point remains in constant spatial relation to the object of interest at least during the relative movement; or
   ii) the at least one camera is temporarily fixedly mounted in relation to the object of interest; and the at least one reference point remains in known spatial relation to the X-ray source and/or the X-ray detector during the relative movement.

4. X-ray imaging system according to claim 1, wherein for the alignment movement of the X-ray source and/or the X-ray detector in relation to the object, the display is configured to display the actual image overlaid with the at least one graphical representation of the at least one reference point in the first image at least successively in a first and a second scale providing an increasing magnification factor for an increasing approximation of alignment.

5. X-ray imaging system according to claim 2, wherein for the acquisition of further X-ray images:
   for a first approximation, a support structure is movable such that the X-ray source and/or the X-ray detector are within a predetermined range of the position of the first projection;
   wherein the support structure comprises at least one movable joint with detectable joint positions and is movable to a predetermined range of matching joint positions in a second approximation; and
   wherein the display is configured to display at least the graphical representation of the reference point in the first image overlaid with the actual image for the alignment as a third approximation.

6. X-ray imaging system according to claim 1, wherein
   i) at least two reference points are provided; or
   ii) at least three reference points are provided.

7. X-ray imaging system according to claim 1, wherein the at least one reference point is provided:
   on the object of interest; and/or
   on a reference field provided in an examination room.

8. X-ray imaging system according to claim 1, wherein the at least one reference point is provided as a laser projection.

9. X-ray imaging system according to claim 1, wherein sensors are provided for detecting a degree of the relative movement that is not detectable by the camera.

10. X-ray imaging system according to claim 1, wherein the camera is provided with
- a light source for acquiring images in a dark environment; and/or
- a wide-angle lens for acquiring image in a surrounding area of the reference point.

11. X-ray imaging system according to claim 1, wherein, for the alignment movement, the X-ray source and/or the X-ray detector are movable in relation to the object in at least two movement directions;
- wherein first movement direction indicators are provided on the X-ray source and/or the X-ray detector visible to the user to indicate possible movement directions in relation to the object; and
- wherein on the display, second movement direction indicators are provided in relation to the displayed image data of the object to indicate the possible movement directions of the image acquisition arrangement in relation to the object.

12. X-ray imaging system according to claim 11, wherein the first movement direction indicators can be provided for a movement plane, wherein the first movement direction indicators are provided as a planar orientation coding, such as a) clock positions, and/or b) cardinal directions; and/or c) colours on a chromatic circle.

13. A method for alignment in X-ray imaging, comprising the following steps:
a) acquiring a first image of at least one reference point with at least one camera;
b) acquiring a first X-ray image of the object of interest with first projection parameters in relation to the object; wherein the projection parameters relate to different degrees of freedom and comprise at least one of the group of spatial projection position, distance to the object, viewing direction or projection angle, and viewing field;
c) relating the first image to the first projection parameters of the first X-ray image in relation to the object;
d) acquiring an actual image with the at least one camera;
e) displaying at least a graphical representation of the at least one reference point in the first image at least partly overlaid with the actual image for guiding an alignment movement of the X-ray source and/or the X-ray detector and the object in relation to each other after an intermediate displacement; and
f) aligning moving of the X-ray source and/or the X-ray detector and the object in relation to each other for an acquisition of at least one further X-ray image in a projection coincident with the first projection parameters of the first X-ray image after an intermediate displacement, based on the displayed overlaid images; wherein either:
i) the at least one camera is fixedly mounted in relation to the X-ray source and/or the X-ray detector; and the at least one reference point remains in constant spatial relation to the object of interest at least during the relative movement;
or wherein:
ii) the at least one camera is temporarily fixedly mounted in relation to the object of interest; and the at least one reference point remains in constant spatial relation to the X-ray source and/or the X-ray detector during the relative movement.

14. A non-transitory computer readable medium, having stored thereon a computer program element, which when being executed by a processing unit, is adapted to perform the method of claim 13.

* * * * *